United States Patent [19]
Müller et al.

[11] Patent Number: 5,639,880
[45] Date of Patent: Jun. 17, 1997

[54] PREPARATION OF AMINE OXIDES

[75] Inventors: Ulrich Müller, Neustadt; Klemens Massonne, Westheim; Karsten Eller; Michael Schulz, both of Ludwigshafen, all of Germany

[73] Assignee: BASF Aktiengesellschaft, Ludwigshafen, Germany

[21] Appl. No.: 656,412

[22] Filed: May 30, 1996

[51] Int. Cl.$^6$ .................... C07C 209/00; C07D 295/24
[52] U.S. Cl. .................... 544/173; 546/184; 548/542; 564/297; 564/298; 564/299
[58] Field of Search .................... 544/173; 546/184; 548/542; 564/298, 297, 299

[56] References Cited

U.S. PATENT DOCUMENTS

| | | | |
|---|---|---|---|
| 4,410,501 | 10/1983 | Taramasso et al. | 423/326 |
| 4,565,891 | 1/1986 | Correa et al. | 564/298 |
| 4,994,614 | 2/1991 | Bauer . | |
| 5,055,233 | 10/1991 | Borland . | |
| 5,082,600 | 1/1992 | Smith . | |
| 5,130,488 | 7/1992 | Smith . | |
| 5,218,116 | 6/1993 | Neri et al. | 544/106 |

FOREIGN PATENT DOCUMENTS

| | | |
|---|---|---|
| 0092862 | 2/1983 | European Pat. Off. . |
| 0307184A3 | 3/1989 | European Pat. Off. . |
| 0320694A3 | 6/1989 | European Pat. Off. . |
| 0401503A3 | 12/1990 | European Pat. Off. . |
| 0426084A1 | 5/1991 | European Pat. Off. . |
| 0553552A3 | 8/1993 | European Pat. Off. . |
| 4306609A1 | 9/1994 | Germany . |

OTHER PUBLICATIONS

(13) Riley, "Ruthenium Chloride Catalysed Oxidation of Tert. Amines to Amine Oxides with Molecular Oxygen", J. Chem. Soc. Chem. Comm. (1983), pp. 1530–1532.

*Primary Examiner*—Peter O'Sullivan
*Attorney, Agent, or Firm*—John H. Shurtleff

[57] ABSTRACT

A process for preparing amine oxides of the general formula I

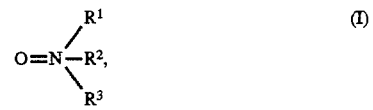

where $R^1$, $R^2$ and $R^3$ are each $C_1$–$C_{30}$-alkyl, $C_3$–$C_{12}$-cycloalkyl, $C_1$–$C_{30}$-hydroxyalkyl, $C_1$–$C_{30}$-aminoalkyl, $C_2$–$C_{30}$-alkoxyalkyl, aryl, $C_7$–$C_{20}$-aralkyl, $C_7$–$C_{20}$-alkylaryl, $C_1$–$C_8$-alkyl-, $C_1$–$C_8$-alkoxy- or halogen-monosubstituted, -disubstituted, -trisubstituted, -tetrasubstituted or -pentasubstituted $C_3$–$C_{12}$-cycloalkyl, aryl, $C_7$–$C_{20}$-aralkyl, $C_7$–$C_{20}$-alkylaryl, —[(CH$_2$)$_2$—O]$_n$—R$^4$, —{[CH(CH$_3$)CH$_2$]—O}$_m$—R$^5$, or $R^1$ and $R^2$ are together an uninterrupted or oxygen-, nitrogen- or sulfur-interrupted $C_3$–$C_{12}$-alkylene diradical chain $R^4$ and $R^5$ are each $C_1$–$C_{12}$-alkyl, $C_3$–$C_{12}$-cycloalkyl, hydroxyl, —COR$^6$ or —CH$_2$—COOR$^7$, $C_3$–$C_{12}$-cycloalkyl, aryl, $C_7$–$C_{20}$-aralkyl or $C_7$–$C_{20}$-alkylaryl, $R^6$ and $R^7$ are each $C_1$–$C_{12}$-alkyl or $C_3$–$C_{12}$-cycloalkyl, and m and n are each from 1 to 40, from amines of the general formula II

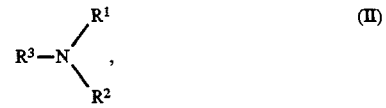

where $R^1$, $R^2$ and $R^3$ are each as defined above, using hydrogen/oxygen mixtures at temperatures from (−5°) to 90° C. and pressures from 1 to 100 bar in the presence of oxidation catalysts comprises using as oxidation catalysts those of group VIII of the periodic table on titanium silicates, vanadium silicates or their mixtures with a zeolite structure.

10 Claims, No Drawings

PREPARATION OF AMINE OXIDES

The present invention relates to a process for preparing amine oxides by reacting amines with hydrogen/oxygen mixtures in the presence of oxidation catalysts of the elements of group VIII of the periodic table on titanium silicates, vanadium silicates or mixtures thereof with a zeolite structure.

The preparation of trialkylamine oxides by reacting the corresponding amines with hydrogen peroxide is known in water as solvent from U.S. Pat. No. 4,994,614, EP-A-320 694 and EP-A-426 084 and in organic solvents or mixtures thereof from EP-A-553 552, EP-A-401 503, U.S. Pat. Nos. 5,055,233, 5,082,600, 5,130,488 and EP-A-307 184. DE-A-43 06 609 discloses the polymer-analogous reaction of polyvinylpyridine to form polyvinylpyridine N-oxides.

A disadvantage with the process described is the use of the costly hydrogen peroxide.

It is an object of the present invention to remedy the aforementioned disadvantages, more particularly to find a way of preparing trialkylamine oxides without having to use hydrogen peroxide.

We have found that this object is achieved by a novel and improved process for preparing amine oxides of the general formula I

where $R^1$, $R^2$ and $R^3$ are each $C_1$–$C_{30}$-alkyl, $C_3$–$C_{12}$-cycloalkyl, $C_1$–$C_{30}$-hydroxyalkyl, $C_1$–$C_{30}$-aminoalkyl, $C_2$–$C_{30}$-alkoxyalkyl, aryl, $C_7$–$C_{20}$-aralkyl, $C_7$–$C_{20}$-akylaryl, $C_1$–$C_8$-alkyl-, $C_1$–$C_8$-alkoxy- or halogen-monosubstituted, -disubstituted, -trisubstituted, -tetrasubstituted or -pentasubstituted $C_3$–$C_{12}$-cycloalkyl, aryl, $C_7$–$C_{20}$-aralkyl, $C_7$–$C_{20}$-alkylaryl, —[(CH$_2$)$_2$—O]$_n$—R$^4$, —{[CH(CH$_3$)CH$_2$]—O}$_m$—R$^5$, or $R^1$ and $R^2$ are together an uninterrupted or oxygen-, nitrogen- or sulfur-interrupted $C_3$–$C_{12}$-alkylene diradical chain $R^4$ and $R^5$ are each $C_1$–$C_{12}$-alkyl, $C_3$–$C_{12}$-cycloalkyl, hydroxyl, —COR$^6$ or —CH$_2$—COOR$^7$, $C_3$–$C_{12}$-cycloalkyl, aryl, $C_7$–$C_{20}$-aralkyl or $C_7$–$C_{20}$-alkylaryl, $R^6$ and $R^7$ are each $C_1$–$C_{12}$-alkyl or $C_3$–$C_{12}$-cycloalkyl, and m and n are each from 1 to 40, from amines of the general formula II

where $R^1$, $R^2$ and $R^3$ are each as defined above, using hydrogen/oxygen mixtures at temperatures from (−5°) to 90° C. and pressures from 1 to 100 bar in the presence of oxidation catalysts, which comprises using as oxidation catalysts those of group VIII of the periodic table on titanium silicates, vanadium silicates or their mixtures with a zeolite structure.

The process of the present invention can be carried out as follows:

The reactor used is preferably a pressure apparatus, for example a pressure vessel such as an autoclave, a sealed shaker or a fixed bed reactor, particularly preferably an autoclave or a pressure-stable steel reactor; the initial charge can be an amine II, without or preferably in an inert solvent, and the oxidation catalyst, preferably a heterogeneous catalyst; and the reaction with a hydrogen/oxygen mixture can be carried out at temperatures from (−5°) to 90° C., preferably 15° to 80° C., particularly preferably 20° to 75° C., and pressures (total pressures) from 1 to 100 bar, preferably 5 to 80 bar, particularly preferably 10 to 70 bar.

Depending on the amine II to be converted, the oxidation of the present invention can be carried out in liquid phase, in the gas phase or else in supercritical phase. In the case of liquids the catalyst is preferably used in the form of a suspension, while in the case of a gas phase or supercritical procedure a fixed bed arrangement is of advantage.

A liquid phase oxidation is generally carried out at a pressure from 1 to 50 bar, advantageously 1 to 10 bar, and in suspension in the presence of solvents. Suitable solvents include alcohols, for example methanol, ethanol, isopropanol or tert-butanol, ketones, for example acetone, diethyl ketone or methyl isobutyl ketone, nitriles such as acetonitrile, mixtures thereof and in particular water. It is also possible to use mixtures of said solvents with water. In certain cases, the use of water or water-containing solvent systems brings about a distinct increase in the selectivity for the desired amine oxide compared with the pure alcohols as solvents.

The molar ratio of oxygen to hydrogen can normally be within the range of $O_2$:$H_2$ from 50:1 to 1:1, preferably 10:1 to 1:1. The molar ratio of amine to oxygen is generally with the range from 1:1 to 3:1, preferably 1.5:1 to 1.7:1. The carrier gas used can be any desired inert gas, nitrogen being particularly suitable.

Suitable oxidation catalysts are those of group VIII of the periodic table of the elements on titanium silicates, vanadium silicates or their mixtures with a zeolite structure, preferably with one or more elements selected from the group consisting of iron, cobalt, nickel, ruthenium, rhodium, palladium, osmium, iridium and platinum, preferably ruthenium, rhodium, palladium, osmium, iridium and platinum, particularly preferably palladium, the oxidation catalysts being such that the platinum metals are in each case present in at least two different bonding energy states.

The proportion of elements of group VIII of the periodic table in the oxidation catalyst of the present invention ranges from 0.01 to 30% by weight, preferably from 0.1 to 15% by weight, in particular from 0.2 to 5% by weight, based on the total mass of the oxidation catalyst, and accordingly the proportion of titanium silicates, vanadium silicates or their mixtures with a zeolite structure is preferably from 99.99 to 70% by weight, particularly preferably from 99.9 to 85% by weight, in particular from 99.8 to 95% by weight.

As well as the platinum metals mentioned, the oxidation catalyst of the present invention may additionally be modified with one or more elements selected from the group consisting of rhenium, silver and gold. These elements are customarily present in an amount from 0.01 to 10% by weight, in particular 0.05 to 5% by weight, based on the total mass of the oxidation catalyst.

The oxidation catalyst should generally be preferably converted before use into the specific modification of the mixture of various bonding energy states.

The various bonding energy states correspond formally to different, ie. two or more, oxidation states of the metals. The bonding energy states are generally different bonding energy states. In a preferred embodiment of the oxidation catalysts of the present invention, the elements of group VIII of the periodic table are present in two, three, four or five, particularly preferably in two, three or four, in particular in two or three, different bonding energy states.

When two different bonding energy states are present this can be for example a mixture of species of oxidation state 0 and (+1), 0 and (+2), 0 and (+3) or 0 and (+4). The two species are normally present in a ratio from 5:95 to 95:5, in particular 10:90 to 90:10.

When three different bonding energy states are present, this can be for example a mixture of species of oxidation state 0, (+1) and (+2) or 0, (+2) and (+3) or 0, (+2) and (+4) or 0, (+1) and (+3) or 0, (+1) and (+4) or 0, (+3) and (+4). The three species are normally present in a ratio from (0.05 to 20):(0.05 to 20):1, in particular (0.1 to 10):(0.1 to 10):1.

It is also possible for mixtures of four or more different oxidation states to be present, for example of 0, (+1), (+2) and (+3) or 0, (+1), (+2) and (+4) or 0, (+2), (+3) and (+4) or 0, (+1), (+3) and (+4) or 0, (+1), (+2), (+3) and (+4). The species are present in this case in similar weight ratios relative to one another as in the mixtures of 2 or 3 different oxidation states.

Of the platinum metals, palladium is preferred. In a particularly preferred embodiment, the palladium is present in two or three different bonding energy states.

The bonding energy states at the surface of the catalyst can most simply be characterized by x-ray photoelectron spectroscopy (XPS). For instance, in a typical mixture of three palladium species, the corresponding values of the energies of the $Pd\ _3P_{5/2}$ state are from 335.0 to 335.4 eV, from 336 to 336.6 eV and 337.1 to 337.9 eV, which formally corresponds to the oxidation states $Pd^0$, $Pd^{1+}$ and $Pd^{2+}$.

In the oxidation catalysts of the present invention it is particularly advantageous to apply the platinum metals in such a way that no metal-metal bonds are formed and metal-zeolite bonds predominate. Analysis of the extended x-ray absorption fine structure, in particular, reveals that, when palladium is present, it is essential that palladium-oxygen bond distances of $2.02\pm9.02$ Å occur almost exclusively and palladium-palladium distances as in extended palladium metal or palladium agglomerates of $2.74\pm0.02$ Å and also palladium-palladium distances of $3.04\pm0.02$ Å as in palladium(II) oxide be avoided.

The oxidation catalyst of the present invention is based on the known titanium or vanadium silicates with a zeolite structure, preferably with a pentasil zeolite structure, in particular the types classified x-rayographically as MFI, MEL or mixed MFI/MEL. Zeolites of this type are described for example in W. M. Meier and D. H. Olson, Atlas of Zeolite Structure Types, Butterworths, 2nd Ed., 1987. Also possible are titanium-containing zeolites having the structure of ZSM-48, ferrierite, beta-zeolite or ZSM-12.

In the oxidation catalyst of the present invention, the titanium of the silicalite can be completely or partially replaced by vanadium. The molar ratio of titanium and/or vanadium to the sum total of silicon plus titanium and/or vanadium is generally within the range from 100:1 to 5:1, preferably 80:1 to 10:1, particularly preferably 60:1 to 20:1.

The oxidation catalyst of the present invention is advantageously prepared by impregnating or reacting titanium or vanadium silicalites having a zeolite structure with salt solutions, chelate complexes or carbonyl complexes of the platinum metals, the required distribution of the bonding energy states of the platinum metals being set following the impregnation or reaction, by suitable reducing or oxidizing conditions.

Thus, the platinum metals can be applied for example by impregnating with a platinum metal salt solution, in particular in oxidation state (+2) to (+4), from a purely aqueous, purely alcoholic or aqueous-alcoholic mixture at temperatures from 20° to 90° C., in particular 30° to 60° C. As salts it is possible to use for example the corresponding chlorides, acetates or their tetramine complexes, suitable in the case of palladium being palladium(II) halides, such as chlorides or bromides, palladium(II) acetate and the palladium(II) tetraminechloro complex. The amount of metal salt used must be such as to produce concentrations from 0.01 to 20% by weight of platinum metal on the resulting oxidation catalyst.

Also possible here is the reaction with corresponding chelate complexes of the platinum metals in apolar solvents, say with acetylacetonates, acetonylacetonates or phosphine complexes. It is also possible to apply the platinum metals in the form of corresponding carbonyl complexes. In this case it is advantageous to work in the gas phase under superatmospheric pressure or to impregnate with these carbonyl complexes in supercritical solvents such as $CO_2$.

Following, if necessary, a drying step and/or, if necessary, a baking step, the resulting catalyst precursor is brought to the desired distribution of the bonding energy states, preferably by partial reduction of higher oxidation states of the platinum metals present, in particular by hydrogenation in a hydrogen atmosphere. If the platinum metals are already present in oxidation state 0, for instance on application as carbonyl complexes, a partial oxidation becomes necessary.

In a preferred embodiment, the oxidation catalyst of the present invention is impregnated with salt solutions of the platinum metals in oxidation state (+2) to (+4) and the dried catalyst is subsequently hydrogenated in a hydrogen atmosphere at temperatures from 20° to 120° C., preferably 25° to 100° C., particularly preferably 30° to 70° C.

If the temperature chosen for this partial reduction by hydrogenation in a hydrogen atmosphere is too high, the platinum metals are almost exclusively present in oxidation state 0, ie. as metals, and in the form of relatively large agglomerates, which is discernible under the microscope as the appearance of metal clusters having sizes above 1 nm.

The aforementioned titanium or vanadium silicalites with a zeolite structure, in particular those having an MFI pentasil zeolite structure, are generally prepared by crystallizing an as-synthesized gel composed of water, a titanium or vanadium source and silicon dioxide in a suitable manner in the presence of organic nitrogen-containing compounds (template compounds) under hydrothermal conditions and optionally in the presence of ammonia, alkali or fluoride as mineralizers. Examples of suitable organic nitrogen-containing compounds are 1,6-diaminohexane or salts or the free hydroxide of tetraalkylammonium, specifically of tetrapropylammonium.

In the preparation of the titanium or vanadium silicalites, it is necessary to avoid any contamination with major quantities of alkali metal or alkaline earth metal compounds; alkali metal contents (in particular of sodium or potassium) <100 ppm are desirable in order that a sufficiently active oxidation catalyst may be obtained later. The crystallization of the single-phase structure of the titanium or vanadium silicalite preferably takes place at temperatures from 140° to 190° C., in particular 160° to 180° C., within a period from 2 to 7 days, a perfectly crystalline product being obtained after about 4 days. Vigorous stirring and a high pH from 12 to 14 during the crystallization can distinctly reduce the synthesis time on the one hand and the crystallite size on the other.

Of advantage are for example primary crystallites from 0.05 to 0.5 μm, but in particular those having sizes of less than 0.2 μm in the average particle diameter.

After crystallization the titanium or vanadium silicalite can be conventionally filtered off, washed and dried at from 100° to 120° C.

To remove the amine or tetraalkylammonium compounds still present in the pores, the material may additionally be subjected to a thermal treatment in air or under nitrogen, in which case it is advantageous to effect the burning off of the template under conditions which limit the temperature rise to values<550° C.

To modify the oxidation catalyst of the present invention, not only the abovementioned additions of platinum metals and other elements may be used but also the conventional techniques of forming with the aid of a binder, ion exchange and surface modification, for example via chemical vapor deposition (CVD) or chemical derivatization such as, say, silylation. The presence of the catalyst functions required for an oxidation reaction can be checked by IR spectroscopy; significant bands indicating the presence of the desired solid state crystallinity and of the oxidation activity required occur at 550 cm$^{-1}$ and at 960 cm$^{-1}$.

Regeneration of the oxidation catalysts of the present invention is likewise possible. Deactivated catalysts can be returned back into an active form by controlled burnoff of carbon deposits within the temperature range from 350° to 650° C. and subsequent reduction, for example with hydrogen.

If carbon deposits are minimal, the catalyst can also be regenerated by a simple wash process. According to requirements, the wash process can be carried out in the neutral, acid or basic pH range. If desired, catalyst activity can also be restored by means of a hydrogen peroxide solution in a mineral acid.

The substituents $R^1$, $R^2$, $R^3$, $R^4$, $R^5$, $R^6$ and $R^7$ and the indices m and n in the compounds I and II have the following meanings:

$R^1$, $R^2$, $R^3$, $R^4$, $R^5$, $R^6$, $R^7$:
  $C_3$–$C_{12}$-cycloalkyl, preferably $C_3$–$C_8$-cycloalkyl such as cyclopropyl, cyclobutyl, cyclopentyl, cyclohexyl, cycloheptyl and cyclooctyl, particularly preferably cyclopentyl, cyclohexyl and cyclooctyl, $R^1$, $R^2$, $R^3$, $R^4$, $R^5$:
  aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $C_7$–$C_{20}$-alkylaryl, preferably $C_7$–$C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $R^1$, $R^2$, $R^3$:
  $C_1$–$C_{30}$-alkyl, preferably $C_1$–$C_{20}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl, isododecyl, n-tetradecyl, n-hexadecyl and n-octadecyl, particularly preferably methyl, ethyl, n-propyl, isopropyl, n-butyl, isobutyl, sec-butyl, tert-butyl, n-octyl, n-decyl, n-dodecyl, n-tetradecyl, n-hexadecyl and n-octadecyl, $C_1$–$C_{30}$-hydroxyalkyl, preferably $C_1$–$C_8$-hydroxyalkyl, particularly preferably $C_1$–$C_4$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxymethylethyl, $C_1$–$C_{30}$-Aminoalkyl, preferably $C_1$–$C_{20}$-aminoalkyl, particularly preferably $C_1$–$C_8$-aminoalkyl such as aminomethyl, 1-aminoethyl, 2-aminoethyl, 1-amino-n-propyl, 2-amino-n-propyl, 3-amino-n-propyl and 1-aminomethylethyl, $C_2$–$C_{30}$-alkoxyalkyl, preferably $C_2$–$C_{20}$-alkoxyalkyl, particularly preferably $C_2$–$C_8$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, $C_1$–$C_8$-alkyl-, $C_1$–$C_8$-alkoxy- or halogen-monosubstituted, -disubstituted, -trisubstituted, -tetrasubstituted or -pentasubstituted $C_3$–$C_{12}$-cycloalkyl, preferably $C_1$–$C_4$-alkyl-, $C_1$–$C_4$-alkoxy- or halogen-monosubstituted, -disubstituted or -trisubstituted $C_3$–$C_8$-cycloalkyl, particularly preferably $C_1$–$C_2$-alkyl-, $C_1$–$C_2$-alkoxy- or halogen-monosubstituted, -disubstituted or -trisubstituted $C_5$–$C_8$-cycloalkyl, $C_1$–$C_8$-alkyl-, $C_1$–$C_8$-alkoxy- or halogen-monosubstituted, -disubstituted, -trisubstituted, -tetrasubstituted or -pentasubstituted aryl, preferably $C_1$–$C_4$-alkyl-, $C_1$–$C_4$-alkoxy- or halogen-monosubstituted, -disubstituted or -trisubstituted phenyl, particularly preferably $C_1$–$C_2$-alkyl-, $C_1$–$C_2$-alkoxy- or halogen-monosubstituted, -disubstituted or -trisubstituted phenyl, $C_1$–$C_8$-alkyl-, $C_1$–$C_8$-alkoxy- or halogen-monosubstituted, -disubstituted, -trisubstituted, -tetrasubstituted or -pentasubstituted $C_7$–$C_{20}$-aralkyl, preferably $C_1$–$C_4$-alkyl-, $C_1$–$C_4$-alkoxy- or halogen-monosubstituted, -disubstituted or -trisubstituted $C_7$–$C_{16}$-phenalkyl, particularly preferably $C_1$–$C_2$-alkyl-, $C_1$–$C_2$-alkoxy- or halogen-monosubstituted, -disubstituted or -trisubstituted $C_7$–$C_{12}$-phenalkyl, $C_1$–$C_8$-alkyl-, $C_1$–$C_8$-alkoxy- or halogen-monosubstituted, -disubstituted, -trisubstituted, -tetrasubstituted or -pentasubstituted $C_7$–$C_{20}$-alkylaryl, preferably $C_1$–$C_4$-alkyl-, $C_1$–$C_4$-alkoxy- or halogen-monosubstituted, -disubstituted or -trisubstituted $C_7$–$C_{16}$-alkylphenyl, particularly preferably $C_1$–$C_2$-alkyl-, $C_1$–$C_2$-alkoxy- or halogen-monosubstituted, -disubstituted or -trisubstituted $C_7$–$C_{12}$-alkylphenyl, —[(CH$_2$)$_2$—O]$_n$—R$^4$, —{[CH(CH$_3$)CH$_2$]—O}$_m$—R$^5$, $R^1$ and $R^2$ together:
  a $C_3$–$C_{12}$-alkylene diradical chain such as —(CH$_2$)$_3$—, —[(CH$_3$)CH—CH$_2$]—, —(CH$_2$)$_4$—, —[CH$_2$—(CH$_3$)CH—CH$_2$]—, —[(CH$_3$)CH—(CH$_2$)$_2$]—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$— and —(CH$_2$)$_{12}$—, preferably a $C_3$–$C_8$-alkylene diradical chain such as —(CH$_2$)$_3$—, —[(CH$_3$)CH—CH$_2$]—, —(CH$_2$)$_4$—, —[CH$_2$—(CH$_3$)CH—CH$_2$]—, —[(CH$_3$)CH—(CH$_2$)$_2$]—, —(CH$_2$)$_5$—, —(CH$_2$)$_6$—, —(CH$_2$)$_7$— and —(CH$_2$)$_8$—, an oxygen-, nitrogen- or sulfur-interrupted $C_3$-$C_{12}$-alkylene diradical chain, preferably an oxygen- or nitrogen-interrupted $C_3$-$C_8$-alkylene diradical chain, particularly preferably an oxygen- or nitrogen-interrupted $C_4$-$C_6$-alkylene diradical chain —[(CH$_2$)$_2$—N—(CH$_2$)$_2$]—,
—[(CH$_2$)$_2$—O—(CH$_2$)$_2$]—,
—[(CH$_2$)$_3$—N—(CH$_2$)$_2$]—,
—[(CH$_2$)$_3$—O—(CH$_2$)$_2$]—,
—[(CH$_2$)$_4$—N—(CH$_2$)$_2$]—,
—[(CH$_2$)$_4$—O—(CH$_2$)$_2$]—,
—[(CH$_2$)$_3$—N—(CH$_2$)$_3$]— and
—[(CH$_2$)$_3$—O—(CH$_2$)$_3$]—, $R^4$ and $R^5$:
  hydroxyl,
  —$COR^6$, or
  —$CH_2$—$COOR^7$, $R^4$, $R^5$, $R^6$ and $R^7$:
  $C_1$-$C_{12}$-alkyl, preferably $C_1$-$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$-$C_4$-alkyl such as methyl, ethyl, n-propyl, isopropyl, n-butyl, isobutyl, sec-butyl and tert-butyl and m and n:
  an integer from 1 to 40, preferably from 2 to 20 such as 2, 3, 4, 5, 6, 7, 8, 9, 10, 11, 12, 13, 14, 15, 16, 17, 18, 19 and 20, particularly preferably from 3 to 15 such as 3, 4, 5, 6, 7, 8, 9, 10, 11, 12, 13, 14 and 15.

Similarly, a polymer-analogous reaction can be used to convert, for example, polyalkylene amines into the corresponding polyalkylene amine N-oxides. This also applies to polymeric pyridines, for example the conversion of polyvinylpyridine into polyvinylpyridine N-oxide.

Typical examples of amine II are dimethyloctylamine, diethyloctylamine, dimethylbutylamine, diethylhexylamine, dimethylisobutylamine, diethyl-2-ethylhexylamine, dimethyldecylamine, dimethyldodecylamine, dimethyltetradecylamine, dimethylhexadecylamine, dimethyloctadecylamine, tributylamine, trimethylamine, butyldiethylamine, triethanolamine, dimethylethanolamine, methyldiethanolamine, dibenzylbutylamine, dicyclohexylmethylamine, N-methylmorpholine, N-butylmorpholine, N-methylpiperidine, N-butylpyrrolidine.

Preference is given to those amines II which contain two short-chain alkyl radicals such as methyl and ethyl besides a long-chain radical having 6 to 20 carbon atoms, for example dimethyloctylamine, dimethyldecylamine, dimethyldodecylamine, dimethyltetradecylamine, dimethyloctadecylamine or amines whose nitrogen atom is part of a heterocyclic ring, such as butylpiperidine or propylpyrrolidine or methylmorpholine or mixtures thereof.

The process of the present invention is particularly useful for oxidizing N-methylmorpholine to N-methylmorpholine oxide.

Tertiary amine oxides find wide application as chemicals and intermediates (Kirk, Othmer, 4th edition vol. 2 pages 357 et seq.). For instance, the oxides of amines having a long alkyl chain, e.g. dimethyldodecylamine, are ingredients of detergent-active formulations. N-Methylmorpholine N-oxide is a highly suitable solvent for cellulose for manufacturing cellulose fibers (cf. for example DE-A-16 94 048). It is also used as an oxidant in the dihydroxylation of olefins [J. Amer. Chem. Soc. 98 (1976), 1986–87] and thus finds use in intermediate synthesis, for example for pharmaceuticals.

EXAMPLES

Catalyst A

Crystallization of a titanium silicalite

To 455 g of tetraethyl orthosilicate were added, in the course of 30 min, 15 g of tetraisopropyl orthotitanate, followed by 800 g of a 20% strength by weight aqueous tetrapropylammonium hydroxide solution (alkali metal content<10 ppm), 1 hour stirring and distillative removal at from 90° to 100° C. The bottom product was mixed with 1.5 liters of deionized water and held at 175° C. in a stirred autoclave for 92 hours. The cold reaction mixture was centrifuged off, washed neutral with water, dried at 110° C. for 24 hours (resulting weight 149 g) and baked at 500° C. under air for 5 hours to burn off the template still present in the zeolite (calcination loss: 14% by weight).

The product was subjected to a wet-chemical analysis and found to have a Ti content of 1.5% by weight and a residual alkali metal (potassium) content of below <0.01% by weight. The yield (calculated on $SiO_2$ used) was 97%. The crystallite size was about 0.1–0.15 μm and the product had characteristic IR bands at 960 $cm^{-1}$ and 550 $cm^{-1}$.

Catalyst B

Application of the active component

A solution of 0.515 g of palladium(II) chloride and 120 g of ammonia solution (25% strength by weight in water) was added to 60 g of the freshly prepared titanium silicate from catalyst A in 130 g of deionized water, stirred for 1 hour and evaporated at from 90° to 100° C./5 mbar. The product was used directly for reduction.

Activation of catalyst B

In a rotary tube oven (quartz glass, diameter 5 cm, heating zone length 20 cm) 20 g of the Pd-impregnated product were reduced in the course of 90 min at a temperature of 50° C. using a gas mixture of 20 l/h of nitrogen and 1 l/h of hydrogen at an oven speed of 50 rpm. A transmission electron micrograph (TEM) of the finished product showed no metallic palladium clusters having sizes above 1.0 nm. The palladium content was found by wet-chemical analysis to be 0.49% by weight. XPS found the three aforementioned binding energy states of the Pd $^{D}5/2$ photoelectron [formally corresponding to the oxidation states (+2), (+1) and 0]. EXAFS measurements on this sample showed a signal for Pd-O or Pd-N bond distances of 2.02±0.02 Å. Pd-Pd bond distances of 2.74±0.02 Å or 3.04±0.02 Å were not observed.

Example 1

In an autoclave, 3.66 g of N-methylmorpholine, 141.3 ml of distilled water and 2 g of catalyst B were stirred at room temperature and 20 bar of oxygen and 20 bar of hydrogen at 30° C. for 2 hours. After decompression, removal of the catalyst by centrifugation and washing of the catalyst, the level of N-methylmorpholine and N-methylmorpholine oxide in the exit stream and wash solution was determined by titration with 1N hydrochloric acid. The results are shown in Table 1.

TABLE 1

|  | Mass [g] | N-Methylmorpholine [% by weight] | N-Methylmorpholine oxide [% by weight] |
|---|---|---|---|
| Product solution | 147.3 | 2.03 | 0.3 |
| Wash solution | 98.1 | 0.07 | 0 |

N-Methylmorpholine conversion: 16.5%
Selectivity: 62%
N-Methylmorpholine oxide yield: 10.4%

Example 2

Example 1 was repeated with 5 g of N-methylmorpholine using a reaction temperature of 60° C. and a reaction time of 5 hours. The results are shown in Table 2.

TABLE 2

|  | Mass [g] | N-Methylmorpholine [% by weight] | N-Methylmorpholine oxide [% by weight] |
|---|---|---|---|
| Product solution | 148.1 | 0 | 2.7 |
| Wash solution | 57.5 | 0.03 | 0 |

N-Methylmorpholine conversion: 98%
Selectivity: 73%
N-Methylmorpholine oxide yield: 72%

Example 3

In an autoclave, 144 ml of distilled water, 15 g of N-methylporpholine and 6 g of catalyst B were stirred at room temperature and 20 bar oxygen and 20 bar of hydrogen at 30° C. for 5 hours. After decompression, removal of the catalyst by centrifugation and washing of the catalyst, the level of N-methylmorpholine and N-methylmorpholine oxide in the exit stream and wash solution was determined by titration with 1N hydrochloric acid. The results are shown in Table 3.

TABLE 3

|  | Mass [g] | N-Methylmorpholine [% by weight] | N-Methylmorpholine oxide [% by weight] |
|---|---|---|---|
| Product solution | 148.5 | 2.5 | 4.53 |
| Wash solution | 67.5 | 0.17 | 0.34 |

N-Methylmorpholine conversion: 74%
Selectivity: 54%
N-Methylmorpholine oxide yield: 40%

Example 4

Example 3 was repeated with 6.5 g of catalytst B. The reaction time was 8 hours. The results are summarized in Table 4.

TABLE 4

|  | Mass [g] | N-Methylmorpholine [% by weight] | N-methylmorpholine oxide [% by weight] |
|---|---|---|---|
| Product solution | 145.5 | 1.2 | 5.63 |
| Wash solution | 62.2 | 0.17 | 0.66 |

N-Methylmorpholine conversion: 88%
Selectivity: 57%
N-Methylmorpholine oxide yield: 50%

Comparative Example I

An autoclave was charged with 144 ml of distilled water, 11 g of N-methylmorpholine and 4.5 g of (5% of Pd on carbon), 20 bar of oxygen and 20 bar of hydrogen were successively injected at room temperature, and the contents were stirred at 60° C. for 8 hours. After cooling and decompression the catalyst was centrifuged off and washed with water. Exit stream and wash solution were titrated with 1N hydrochloric acid. The results are shown in Table I.

TABLE I

|  | Mass [g] | N-Methylmorpholine [% by weight] | N-Methylmorpholine oxide [% by weight] |
|---|---|---|---|
| Product solution | 136.9 | 7.7 | 0 |
| Wash solution | 80.3 | 0.49 | 0 |

Comparative Example II

Example I was repeated with 5 g of N-methylmorpholine and 2 g of catalyst A (titanium silicalite) at a reaction temperature of 30° C. using a reaction time of 2 hours. The result are shown in Table II.

TABLE II

|  | Mass [g] | N-Methylmorpholine [% by weight] | N-Methylmorpholine oxide [% by weight] |
|---|---|---|---|
| Product solution | 148 | 2.91 | 0 |
| Wash solution | 53.7 | <0.1 | 0 |

We claim:

1. A process for preparing amine oxides of the general formula I

where

R$^1$, R$^2$ and R$^3$ are each $C_1$–$C_{30}$-alkyl, $C_3$–$C_{12}$-cycloalkyl, $C_1$–$C_{30}$-hydroxyalkyl, $C_1$–$C_{30}$-aminoalkyl, $C_2$–$C_{30}$-alkoxyalkyl, aryl, $C_7$–$C_{20}$-aralkyl, $C_7$–$C_{20}$-alkylaryl, $C_1$–$C_8$-alkyl-, $C_1$–$C_8$-alkoxy- or halogen-monosubstituted, -disubstituted, -trisubstituted, -tetrasubstituted or pentasubstituted $C_3$–$C_{12}$-cycloalkyl, aryl, $C_7$–$C_{20}$-aralkyl, $C_7$–$C_{20}$-alkylaryl, —[($CH_2$)$_2$—O]$_n$—R$^4$, —{[CH(CH$_3$)CH$_2$]—O}$_m$—R$^5$, or R$^1$ and R$^2$ are together an interrupted or oxygen-, nitrogen- or sulfur-interrupted $C_3$–$C_{12}$-alkylene diradical chain $R^4$ and $R^5$ are each $C_1$–$C_{12}$-alkyl, $C_3$–$C_{12}$-cycloalkyl, hydroxl, —$COR^6$ or —$CH_2$—$COOR^7$, $C_3$–$C_{12}$-cycloalkyl, aryl, $C_7$–$C_{20}$-aralkyl or $C_7$–$C_{20}$-alkylaryl, $R^6$ and $R^7$ are each $C_1$–$C_{12}$-alkyl or $C_3$–$C_{12}$-cycloalkyl, and m and n are each from 1 to 40, from amines of the general formula II

where $R^1$, $R^2$ and $R^3$ are each as defined above, using hydrogen/oxygen mixtures at temperatures from (−5°) to 90° C. and pressures from 1 to 100 bar in the presence of oxidation catalysts, which comprises using as oxidation catalysts those of group VIII of the periodic table on titanium silicates, vanadium silicates or their mixtures with a zeolite structure.

2. A process for preparing amine oxides I as claimed in claim 1, wherein the oxidation catalysts include from 0.01 to 20% by weight of the elements of group VIII of the periodic table.

3. A process for preparing amine oxides I as claimed in claim 1, wherein the oxidation catalysts include as elements of group VIII of the periodic table ruthenium, rhodium, palladium, osmium, iridium, platinum or mixtures thereof.

4. A process for preparing amine oxides I as claimed in claim 1, wherein the oxidation catalysts additionally include one or more elements selected from the group consisting of rhenium, silver and gold.

5. A process for preparing amine oxides I as claimed in claim 1, wherein the oxidation catalysts contain from 0.01 to 20% by weight of the elements group VIII of the periodic table and from 99.99 to 80% by weight of titanium silicates, vanadium silicates or their mixtures with a zeolite structure.

6. A process for preparing amine oxides I as claimed in claim 1, wherein the elements of group VIII of the periodic table are present in at least two different bonding energy states.

7. A process for preparing amine oxides I as claimed in claim 1, wherein the oxidation catalysts include as elements of group VIII of the periodic table palladium which is present in two or three different bonding energy states.

8. A process for preparing amine oxides I as claimed in claim 1, wherein the molar ratio of silicon to titanium, vanadium or mixtures thereof in the oxidation catalyst is from 100:1 to 5:1.

9. A process for preparing amine oxides I as claimed in claim 1, wherein $R^1$, $R^2$ and $R^3$ are each $C_1$–$C_4$-alkyl, $R^1$ and $R^2$ are together —$(CH_2)_2$—O—$(CH_2)_2$— or —$(CH_2)_2$—$NR^1$—$(CH_2)_2$—, and $R^3$ is additionally n-decyl, n-dodecyl, n-tetradecyl, n-hexadecyl or n-octadecyl.

10. A process for preparing amine oxides I as claimed in claim 1, wherein $R^1$ and $R^2$ are together —$(CH_2)_2$—O—$(CH_2)_2$— and $R^3$ is methyl.

* * * * *

UNITED STATES PATENT AND TRADEMARK OFFICE
CERTIFICATE OF CORRECTION

PATENT NO. : 5,639,880

DATED : Jun. 17, 1997

INVENTOR(S) : Mueller et al

It is certified that error appears in the above-indentified patent and that said Letters Patent is hereby corrected as shown below:

On the title page,

Under "[57] ABSTRACT", cancel the original text in its entirety and substitute:

--A process for preparing a tertiary amine oxide by a catalytic oxidation of the corresponding tertiary amine wherein a hydrogen/oxygen gas miture is reacted with the tertiary amine at a temperature of from -5 to 90°C, under a pressure of from 1 to 100 bar and in the presence of an oxidation catalyst in which at least one metal of Group VIII of the Periodic Table is carried on a zeolite support selected from the group consisting of titanium and zirconium silicates and their mixtures having a zeolite structure.--

UNITED STATES PATENT AND TRADEMARK OFFICE
CERTIFICATE OF CORRECTION

PATENT NO. : 5,639,880
DATED : Jun. 17, 1997
INVENTOR(S) : Mueller et al

Page 2 of 2

It is certified that error appears in the above-indentified patent and that said Letters Patent is hereby corrected as shown below:

IN THE CLAIMS, please add the following new claims:

--11. In a process for preparing a tertiary amine oxide by a catalytic oxidation of the corresponding tertiary amine, the improvement which comprises:
  reacting a hydrogen/oxygen gas mixture with said tertiary amine at a temperature of from -5 to 90°C and under a pressure of from 1 to 100 bar in the presence of an oxidation catalyst in which at least one metal of Group VIII of the Periodic Table is carried on a zeolite support selected from the group consisting of titanium and zirconium silicates and their mixtures.--

--12. A process as claimed in Claim 11, wherein the tertiary amine reactant is a trialkyl amine containing from 1 to 20 carbon atoms in each alkyl group.--

--13. A process as claimed in Claim 11, wherein the tertiary amine reactant is trimethylamine.--

--14. A process as claimed in Claim 11, wherein the tertiary amine reactant is triethylamine.--

--15. A process as claimed in Claim 11, wherein the tertiary amine reactant is a heterocyclic amine selected from the group consisting of piperidine, pyrrolidine and morpholine which is N-substituted by alkyl of 1 to 4 carbon atoms.--

--16. A process as claimed in Claim 11, wherein the tertiary amine reactant is N-methylmorpholine.--

Signed and Sealed this

First Day of September, 1998

*Attest:*

BRUCE LEHMAN

*Attesting Officer*  Commissioner of Patents and Trademarks